United States Patent
Abe

(10) Patent No.: US 9,472,828 B2
(45) Date of Patent: Oct. 18, 2016

(54) NONAQUEOUS ELECTROLYTE SOLUTION, ELECTRICITY STORAGE DEVICE USING SAME, AND TRIFLUOROMETHYLBENZENE COMPOUND

(75) Inventor: Koji Abe, Yamaguchi (JP)

(73) Assignee: UBE INDUSTRIES, LTD., Ube-shi (JP)

( * ) Notice: Subject to any disclaimer, the term of this patent is extended or adjusted under 35 U.S.C. 154(b) by 256 days.

(21) Appl. No.: 14/112,778

(22) PCT Filed: Mar. 30, 2012

(86) PCT No.: PCT/JP2012/058566
§ 371 (c)(1),
(2), (4) Date: Oct. 21, 2013

(87) PCT Pub. No.: WO2012/144306
PCT Pub. Date: Oct. 26, 2012

(65) Prior Publication Data
US 2014/0038060 A1    Feb. 6, 2014

(30) Foreign Application Priority Data

Apr. 22, 2011  (JP) ................. 2011-096628

(51) Int. Cl.
| | |
|---|---|
| *H01M 10/0567* | (2010.01) |
| *C07C 69/96* | (2006.01) |
| *H01M 10/0525* | (2010.01) |
| *C07C 309/66* | (2006.01) |
| *C07C 309/73* | (2006.01) |
| *H01M 4/583* | (2010.01) |
| *H01M 4/505* | (2010.01) |
| *H01M 4/525* | (2010.01) |
| *H01M 10/0569* | (2010.01) |

(52) U.S. Cl.
CPC .......... *H01M 10/0567* (2013.01); *C07C 69/96* (2013.01); *C07C 309/66* (2013.01); *C07C 309/73* (2013.01); *H01M 10/0525* (2013.01); *H01M 4/505* (2013.01); *H01M 4/525* (2013.01); *H01M 4/583* (2013.01); *H01M 10/0569* (2013.01); *H01M 2300/0025* (2013.01); *H01M 2300/0034* (2013.01); *Y02E 60/122* (2013.01)

(58) Field of Classification Search
CPC .............. H01M 10/0567; H01M 10/0569; H01M 10/0525; H01M 4/583; H01M 4/505; H01M 4/525; Y02E 60/122; C07C 309/66; C07C 309/73
See application file for complete search history.

(56) References Cited

U.S. PATENT DOCUMENTS

| | | |
|---|---|---|
| 3,906,104 A | 9/1975 | Partos |
| 4,310,656 A | 1/1982 | Brunelle |
| 2007/0054185 A1 | 3/2007 | Abe et al. |
| 2010/0291437 A1 | 11/2010 | Abe et al. |
| 2011/0123871 A1 | 5/2011 | Nakagawa et al. |
| 2012/0189919 A1 | 7/2012 | Abe et al. |

(Continued)

FOREIGN PATENT DOCUMENTS

| | | |
|---|---|---|
| EP | 1 672 729 A1 | 6/2006 |
| EP | 2 249 426 A1 | 11/2010 |

(Continued)

OTHER PUBLICATIONS

Kovacic, et al., "Oxygenation of Aromatic Compounds with Diisopropyl Peroxydicarbonate-Cupric Chloride", The Journal of Organic Chemistry, vol. 34, No. 11, pp. 3302-3308, (Feb. 11, 1969).

(Continued)

*Primary Examiner* — Laura Weiner
(74) *Attorney, Agent, or Firm* — Oblon, McClelland, Maier & Neustadt, L.L.P.

(57) ABSTRACT

The present invention is to provide a nonaqueous electrolytic solution capable of enhancing electrochemical characteristics in a broad temperature range, an energy storage device using the nonaqueous electrolytic solution, and a specific trifluoromethylbenzene compound. There are provided a nonaqueous electrolytic solution of an electrolyte salt dissolved in a nonaqueous solvent, which comprises at least one halogenoalkylbenzene compound represented by the following general formula (I), an energy storage device using the nonaqueous electrolytic solution, and a specific trifluoromethylbenzene compound.

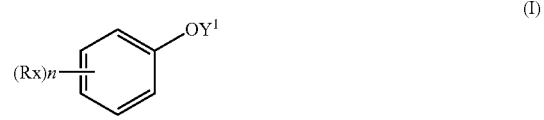

(I)

(In the formula, $Y^1$ represents an alkoxycarbonyl group having from 2 to 8 carbon atoms, an alkenyloxycarbonyl group having from 3 to 9 carbon atoms, an alkynyloxycarbonyl group having from 4 to 9 carbon atoms, an aryloxycarbonyl group having from 7 to 12 carbon atoms, an alkanesulfonyl group having from 1 to 6 carbon atoms, or an arylsulfonyl group having from 6 to 12 carbon atoms; $R_X$ represents a halogenoalkyl group having from 1 to 4 carbon atoms; n indicates an integer of from 1 to 5. However, when $Y^1$ is an alkoxycarbonyl group having from 2 to 12 carbon atoms or an aryloxycarbonyl group having from 6 to 12 carbon atoms, the number of carbon atom of $R_X$ is 1. In the substituent represented by $Y^1$, at least one hydrogen atom may be substituted with a halogen atom.)

20 Claims, No Drawings

(56) References Cited

U.S. PATENT DOCUMENTS

| | | |
|---|---|---|
| 2012/0219854 A1 | 8/2012 | Nakagawa et al. |
| 2012/0308883 A1 | 12/2012 | Nakagawa et al. |
| 2014/0134481 A1 | 5/2014 | Nakagawa et al. |

FOREIGN PATENT DOCUMENTS

| | | |
|---|---|---|
| EP | 2 469 638 A1 | 6/2012 |
| JP | 58-83651 A | 5/1983 |
| JP | 59-1444 A | 1/1984 |
| JP | 2000 106209 | 4/2000 |
| JP | 2002 343424 | 11/2002 |
| JP | 2004-87168 A | 3/2004 |
| JP | 2009 231283 | 10/2009 |
| WO | WO 2011/021570 A1 | 2/2011 |
| WO | 2011 025016 | 3/2011 |

OTHER PUBLICATIONS

International Search Report Issued Jul. 3, 2012 in PCT/JP12/058566 Filed Mar. 30,2002.

Extended European Search Report issued Sep. 12, 2014 in Patent Application No. 12774584.2.

NONAQUEOUS ELECTROLYTE SOLUTION, ELECTRICITY STORAGE DEVICE USING SAME, AND TRIFLUOROMETHYLBENZENE COMPOUND

TECHNICAL FIELD

The present invention relates to a nonaqueous electrolytic solution capable of improving electrochemical characteristics of an energy storage device in a broad temperature range, an energy storage device using it, and a specific trifluoromethylbenzene compound.

BACKGROUND ART

In recent years, energy storage devices, especially lithium secondary batteries have been widely used for small-sized electronic devices, such as mobile telephones, notebook-size personal computers and the like, for electric vehicles, as well as for electric power storage. These electronic devices and vehicles may be used in a broad temperature range, for example, at midsummer high temperatures or at frigid low temperatures, and are therefore required to be improved in point of electrochemical characteristics well balanced in a broad temperature range.

Especially for preventing global warming, it is imperative to reduce $CO_2$ emissions, and of environment-responsive vehicles with, as mounted thereon, an electricity storage installation that comprises an energy storage device, such as a lithium secondary battery, a capacitor or the like, early popularization of hybrid electric vehicles (HEV), plug-in hybrid electric vehicles (PHEV) and battery electric vehicles (BEV) is desired. Vehicles could take a long travel distance and therefore could be used in regions in a broad temperature range covering from extremely-hot tropical regions to frigid regions. In particular, therefore, it is desired that the electrochemical characteristics of in-car energy storage devices for those vehicles are not worsened even in use thereof in a broad temperature range covering from high temperatures to low temperatures.

In this specification, the term, lithium secondary battery is used as a concept including a so-called lithium ion secondary battery.

A lithium secondary battery is mainly constituted of a positive electrode and a negative electrode containing a material capable of absorbing and releasing lithium, and a nonaqueous electrolytic solution containing a lithium salt and a nonaqueous solvent. For the nonaqueous solvent, used are carbonates, such as ethylene carbonate (EC), propylene carbonate (PC), etc.

As the negative electrode, known are metal lithium, and metal compounds (metal elemental substances, oxides, alloys with lithium, etc.) and carbon materials capable of absorbing and releasing lithium. In particular, a lithium secondary battery using a carbon material capable of absorbing and releasing lithium, such as coke, artificial graphite, natural graphite or the like, has been widely put into practical use.

For example, it is known that, in a lithium secondary battery using a highly-crystalline carbon material, such as natural graphite, artificial graphite or the like as the negative electrode material therein, the decomposed products or gas generated through reductive decomposition of the solvent in the nonaqueous electrolytic solution on the surface of the negative electrode during charging detracts from the electrochemical reaction favorable for the battery, therefore worsening the cycle properties of the battery. Deposition of the decomposed products of the nonaqueous solvent interferes with smooth absorption and release of lithium by the negative electrode, and therefore the electrochemical characteristics of the battery in use thereof in a broad temperature range may often tend to worsen.

In addition, it is known that a lithium secondary battery using a lithium metal or its alloy, or a metal elemental substance, such as tin, silicon or the like or its metal oxide as the negative electrode material therein could have a high initial battery capacity but the battery capacity and the battery performance thereof, such as cycle properties may greatly worsen, since the micronized powdering of the material is promoted during cycles thereby bringing about accelerated reductive decomposition of the nonaqueous solvent, as compared with the negative electrode of a carbon material. In addition, the micronized powdering of the negative electrode material and the deposition of the decomposed products of the nonaqueous solvent may interfere with smooth absorption and release of lithium by the negative electrode, and therefore the electrochemical characteristics of the battery in use thereof in a broad temperature range may often tend to worsen.

On the other hand, it is known that, in a lithium secondary battery using, for example, $LiCoO_2$, $LiMn_2O_4$, $LiNiO_2$, $LiFePO_4$ or the like as the positive electrode, the nonaqueous solvent in the nonaqueous electrolytic solution locally undergoes partial oxidative decomposition in the interface between the positive electrode material and the nonaqueous electrolytic solution in the charged state and the decomposed products or the gas thereby generated as a result of the partial oxidative decomposition interferes with the electrochemical reaction favorable for the battery, and therefore the electrochemical characteristics of the battery would be thereby also worsened in use in a broad temperature range.

As in the above, the decomposed products and the gas generated through decomposition of the nonaqueous electrolytic solution on the positive electrode or the negative electrode may interfere with the movement of lithium ions or may swell the battery, and the battery performance is thereby worsened. Despite the situation, electronic appliances equipped with lithium secondary batteries therein are offering more and more an increasing range of functions and are being in a stream of further increase in power consumption. With that, the capacity of lithium secondary batteries is being much increased, and the space volume for the nonaqueous electrolytic solution in the battery is decreased by increasing the density of the electrode and by reducing the useless space volume in the battery. Accordingly, the situation is that even decomposition of only a small amount of the nonaqueous electrolytic solution may worsen the electrochemical characteristics of the battery in use thereof in a broad temperature range.

PTL 1 proposes a nonaqueous electrolytic solution containing methyl phenyl carbonate or 4-t-butylphenyl methyl carbonate, and suggests improving overcharge tolerance and continuous charge performance.

CITATION LIST

Patent Literature

PTL 1: JP-A 2009-231283

SUMMARY OF INVENTION

Technical Problem

An object of the present invention is to provide a nonaqueous electrolytic solution capable of improving electrochemical characteristics in abroad temperature range, an energy storage device using it, and a specific trifluoromethylbenzene compound.

Solution to Problem

The present inventors have investigated in detail the performance of the nonaqueous electrolytic solutions in the above-mentioned prior art. As a result, the current situation is that the nonaqueous electrolytic solution of the above-mentioned PTL 1 could not be said to be sufficiently satisfactory for the problem of improving the electrochemical characteristics of batteries in a broad temperature range, such as low-temperature discharge characteristics thereof after high-temperature storage, etc.

Given the situation, the present inventors have assiduously studied for the purpose of solving the above-mentioned problems, and have found that, when at least one specific compound is added to a nonaqueous electrolytic solution of an electrolyte salt dissolved in a nonaqueous solvent, then the electrochemical characteristics, especially the electrochemical characteristics of lithium batteries in abroad temperature range can be improved, and have completed the present invention.

Specifically, the present invention provides the following (1) to (3):

(1) A nonaqueous electrolytic solution of an electrolyte salt dissolved in a nonaqueous solvent, which comprises at least one halogenoalkylbenzene compound represented by the following general formula (I):

[Chem. 1]

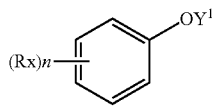

(I)

(In the formula, $Y^1$ represents an alkoxycarbonyl group having from 2 to 8 carbon atoms, an alkenyloxycarbonyl group having from 3 to 9 carbon atoms, an alkynyloxycarbonyl group having from 4 to 9 carbon atoms, an aryloxycarbonyl group having from 7 to 12 carbon atoms, an alkanesulfonyl group having from 1 to 6 carbon atoms, or an arylsulfonyl group having from 6 to 12 carbon atoms; $R_X$ represents a halogenoalkyl group having from 1 to 4 carbon atoms; n indicates an integer of from 1 to 5. However, when $Y^1$ is an alkoxycarbonyl group having from 2 to 12 carbon atoms or an aryloxycarbonyl group having from 6 to 12 carbon atoms, the number of carbon atom of $R_X$ is 1. In the substituent represented by $Y^1$, at least one hydrogen atom may be substituted with a halogen atom.)

(2) An energy storage device comprising a positive electrode, a negative electrode, and a nonaqueous electrolytic solution of an electrolyte salt dissolved in a nonaqueous solvent, wherein the nonaqueous electrolytic solution is the nonaqueous electrolytic solution of the above (1).

(3) A trifluoromethylbenzene compound represented by the following general formula (II):

[Chem. 2]

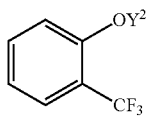

(II)

(In the formula, $Y^2$ represents a linear alkoxycarbonyl group having from 2 to 8 carbon atoms, an alkenyloxycarbonyl group having from 3 to 9 carbon atoms, an alkynyloxycarbonyl group having from 4 to 9 carbon atoms, an aryloxycarbonyl group having from 7 to 12 carbon atoms, an alkanesulfonyl group having from 1 to 6 carbon atoms, or an arylsulfonyl group having from 6 to 12 carbon atoms. In the substituent represented by $Y^2$, at least one hydrogen atom may be substituted with a halogen atom.)

Advantageous Effects of Invention

According to the present invention, there are provided a nonaqueous electrolytic solution capable of improving the electrochemical characteristics of energy storage devices in a broad temperature range, especially the low-temperature discharge characteristics thereof after high-temperature storage, an energy storage device, such as lithium batteries and others using the nonaqueous electrolytic solution, and a specific trifluoromethylbenzene compound.

DESCRIPTION OF EMBODIMENTS

The present invention relates to a nonaqueous electrolytic solution, an energy storage device using it, and a specific trifluoromethylbenzene compound.

(Nonaqueous Electrolytic Solution)

The nonaqueous electrolytic solution of the present invention comprises an electrolyte salt dissolved in a nonaqueous solvent, and comprises at least one halogenoalkylbenzene compound represented by the above-mentioned general formula (I).

Though not always clear, the reason why the nonaqueous electrolytic solution of the present invention can remarkably improve the electrochemical characteristics of energy storage devices in a broad temperature range may be considered as follows: The halogenoalkylbenzene compound represented by the above-mentioned general formula (I) in the present invention has a phenyl group that has a highly-electrophilic functional group, such as an alkoxycarbonyl group, an alkanesulfonyl group or the like and a halogenoalkyl group of a bulky and unremovable electron-attractive group. As having such a highly-electrophilic functional group and an electron attractive group, the decomposability of the compound increases and the compound polymerizes on a negative electrode to give a highly heat-resistant, benzene ring-derived surface film. Further, it is considered that, since the halogenoalkyl group is a bulky and unremovable group, any excessive polymerization of the compound could be prevented and therefore the compound could remarkably improve the low-temperature discharge characteristics of batteries after high-temperature storage, which, however, could not be attained by any other compound merely having a bulky substituent, for example, 4-t-butylphenylmethyl carbonate or by a compound merely having an electron attractive group, for example, (2-fluorophenyl) methyl carbonate.

The halogenoalkylbenzene compound to be contained in the nonaqueous electrolytic solution of the present invention is represented by the following general formula (I):

[Chem. 3]

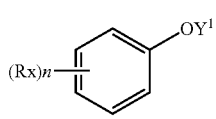

(I)

(In the formula, $Y^1$ represents an alkoxycarbonyl group having from 2 to 8 carbon atoms, an alkenyloxycarbonyl group having from 3 to 9 carbon atoms, an alkynyloxycarbonyl group having from 4 to 9 carbon atoms, an aryloxycarbonyl group having from 7 to 12 carbon atoms, an alkanesulfonyl group having from 1 to 6 carbon atoms, or an arylsulfonyl group having from 6 to 12 carbon atoms; $R_X$ represents a halogenoalkyl group having from 1 to 4 carbon atoms; n indicates an integer of from 1 to 5. However, when $Y^1$ is an alkoxycarbonyl group having from 2 to 12 carbon atoms or an aryloxycarbonyl group having from 6 to 12 carbon atoms, the number of carbon atom of $R_X$ is 1. In the substituent represented by $Y^1$, at least one hydrogen atom may be substituted with a halogen atom.)

In the general formula (I), $R_X$ is preferably a halogenoalkyl group having 1 or 2 carbon atoms, more preferably a fluoroalkyl group having 1 or 2 carbon atoms.

As specific examples of $R_X$, preferably mentioned are a fluoroalkyl group, such as a fluoromethyl group, a difluoromethyl group, a trifluoromethyl group, a 2,2,2-trifluoroethyl group, a perfluoroethyl group, a perfluoropropyl group, a perfluorobutyl group, etc.; a chloroalkyl group, such as a chloromethyl group, a trichloromethyl group, a 2,2,2-trichloroethyl group, etc.; a bromoalkyl group, such as a bromomethyl group, a 2-bromoethyl group, etc. Of those, preferred is a halogenoalkyl group having 1 or 2 carbon atoms, such as a difluoromethyl group, a trifluoromethyl group, a 2,2,2-trifluoroethyl group, a perfluoroethyl group, a chloromethyl group, a trichloromethyl group, a 2,2,2-trichloroethyl group, etc., and more preferred is a fluoroalkyl group having 1 or 2 carbon atoms, such as a difluoromethyl group, a trifluoromethyl group, a 2,2,2-trifluoroethyl group, a perfluoroethyl group, etc.

$Y^1$ is preferably an alkoxycarbonyl group having from 2 to 4 carbon atoms, an alkynyloxycarbonyl group having from 3 to 7 carbon atoms, an aryloxycarbonyl group having from 7 to 10 carbon atoms, an alkanesulfonyl group having from 1 to 4 carbon atoms, or an arylsulfonyl group having from 6 to 10 carbon atoms, and is more preferably an alkoxycarbonyl group having from 2 to 4 carbon atoms, an alkynyloxycarbonyl group having from 3 to 6 carbon atoms, an aryloxycarbonyl group having 7 or 8 carbon atoms, or an alkanesulfonyl group having 1 or 2 carbon atoms.

As specific examples of $Y^1$, preferably mentioned are (a) a linear alkoxycarbonyl group, such as a methoxycarbonyl group, an ethoxycarbonyl group, an n-propoxycarbonyl group, an n-butoxycarbonyl group, an n-pentyloxycarbonyl group, an n-hexyloxycarbonyl group, etc.; (b) a branched alkoxycarbonyl group, such as an iso-propoxycarbonyl group, a sec-butoxycarbonyl group, a tert-butoxycarbonyl group, a tert-amyloxycarbonyl group, etc.; (c) an alkoxycarbonyl group in which the hydrogen atom is partly substituted with a fluorine atom, such as a fluoromethoxycarbonyl group, a trifluoromethoxycarbonyl group, a 2,2,2-trifluoroethoxycarbonyl group, etc.; (d) an alkenyloxycarbonyl group, such as a vinyloxycarbonyl group, a 1-propenyloxycarbonyl group, a 2-propenyloxycarbonyl group, a 1-methyl-2-propenyloxycarbonyl group, a 1,1-dimethyl-2-propenyloxycarbonyl group, a 1-butenyloxycarbonyl group, a 2-butenyloxycarbonyl group, a 3-butenyloxycarbonyl group, a 2-pentenyloxycarbonyl group, a 2-hexenyloxycarbonyl group, etc.; an alkynyloxycarbonyl group, such as a 2-propynyloxycarbonyl group, a 2-butynyloxycarbonyl group, a 3-butynyloxycarbonyl group, a 4-pentynyloxycarbonyl group, a 5-hexynyloxycarbonyl group, a 1-methyl-2-propynyloxycarbonyl group, a 1-methyl-2-butynyloxycarbonyl group, a 1,1-dimethyl-2-propynyloxycarbonyl group, etc.; (e) an aryloxycarbonyl group, such as a phenyloxycarbonyl group, a 2-methylphenyloxycarbonyl group, a 3-methylphenyloxycarbonyl group, a 4-methylphenyloxycarbonyl group, a 4-tert-butylphenyloxycarbonyl group, a 2,4,6-trimethylphenyloxycarbonyl group, a 2-fluorophenyloxycarbonyl group, a 3-fluorophenyloxycarbonyl group, a 4-fluorophenyloxycarbonyl group, a 2,4-difluorophenyloxycarbonyl group, a 2,6-difluorophenyloxycarbonyl group, a 3,4-difluorophenyloxycarbonyl group, a 2,4,6-trifluorophenyloxycarbonyl group, a pentafluorophenyloxycarbonyl group, a 2-trifluoromethylphenyloxycarbonyl group, a 3-trifluoromethylphenyloxycarbonyl group, a 4-trifluoromethylphenyloxycarbonyl group, etc.; (f) a linear alkanesulfonyl group, such as a methanesulfonyl group, an ethanesulfonyl group, a propane-1-sulfonyl group, a butane-1-sulfonyl group, a pentane-1-sulfonyl group, a hexane-1-sulfonyl group, etc.; (g) a branched alkanesulfonyl group, such as a propane-2-sulfonyl group, a butane-2-sulfonyl group, a 2-methylpropane-2-sulfonyl group, a 2-methylbutane-2-sulfonyl group, etc.; (h) an alkanesulfonyl group in which the hydrogen atom is partly substituted with a fluorine atom, such as a fluoromethanesulfonyl group, a trifluoromethanesulfonyl group, a 2,2,2-trifluoroethanesulfonyl group, etc.; (j) an arylsulfonyl group, such as a benzenesulfonyl group, a 2-methylbenzenesulfonyl group, a 3-methylbenzenesulfonyl group, a 4-methylbenzenesulfonyl group, a 4-tert-butylbenzenesulfonyl group, a 2,4,6-trimethylbenzenesulfonyl group, a 2-fluorobenzenesulfonyl group, a 3-fluorobenzenesulfonyl group, a 4-fluorobenzenesulfonyl group, a 2,4-difluorobenzenesulfonyl group, a 2,6-difluorobenzenesulfonyl group, a 3,4-difluorobenzenesulfonyl group, a 2,4,6-trifluorobenzenesulfonyl group, a pentafluorobenzenesulfonyl group, a 4-trifluoromethylbenzenesulfonyl group, etc.

Of those, preferred are (a) a methoxycarbonyl group, an ethoxycarbonyl group, an n-propoxycarbonyl group; (d) a 2-propynyloxycarbonyl group, a 2-butynyloxycarbonyl group, a 3-butynyloxycarbonyl group; (e) a phenyloxycarbonyl group, a 2-methylphenyloxycarbonyl group, a 3-methylphenyloxycarbonyl group, a 4-methylphenyloxycarbonyl group, a 2-trifluoromethylphenyloxycarbonyl group, a 3-trifluoromethylphenyloxycarbonyl group, a 4-trifluoromethylphenyloxycarbonyl group; (f) a methanesulfonyl group, an ethanesulfonyl group, a propane-1-sulfonyl group, a butane-1-sulfonyl group; (j) a benzenesulfonyl group, a 2-methylbenzenesulfonyl group, a 3-methylbenzenesulfonyl group, a 4-methylbenzenesulfonyl group; and more preferred are a methoxycarbonyl group, an ethoxycarbonyl group, a 2-propynyloxycarbonyl group, a 2-trifluoromethylphenyloxycarbonyl group, a methanesulfonyl group and an ethanesulfonyl group.

In the general formula (I), n is preferably from 1 to 4, more preferably 1 or 2.

The compounds where the substituents fall within the above-mentioned ranges are preferred as capable of noticeably improving the electrochemical characteristics of batteries in a broad temperature range.

The effect of improving the electrochemical characteristics in a broad temperature range depends on the position of $R_X$; and preferably, the compound has $R_X$ at the ortho- or para-position thereof, and more preferably has $R_X$ at the ortho-position.

Concrete examples of the halogenoalkylbenzene compound represented by the general formula (I) are mentioned below.

(i) As the case where $Y^1$ is an alkoxycarbonyl group:

Preferably mentioned are methyl (2-trifluoromethylphenyl) carbonate, ethyl (2-trifluoromethylphenyl) carbonate, n-propyl (2-trifluoromethylphenyl) carbonate, n-butyl (2-trifluoromethylphenyl) carbonate, n-pentyl (2-trifluoromethylphenyl) carbonate, n-hexyl (2-trifluoromethylphenyl) carbonate, iso-propyl (2-trifluoromethylphenyl) carbonate, sec-butyl (2-trifluoromethylphenyl) carbonate, tert-butyl (2-trifluoromethylphenyl) carbonate, tert-amyl (2-trifluoromethylphenyl) carbonate, fluoromethyl (2-trifluoromethylphenyl) carbonate, trifluoromethyl (2-trifluoromethylphenyl) carbonate, 2,2,2-trifluoroethyl (2-trifluoromethylphenyl) carbonate, vinyl (2-trifluoromethylphenyl) carbonate, 1-propenyl (2-trifluoromethylphenyl) carbonate, 2-propenyl (2-trifluoromethylphenyl) carbonate, 1-methyl-2-propenyl (2-trifluoromethylphenyl) carbonate, 1,1-dimethyl-2-propenyl (2-trifluoromethylphenyl) carbonate, 1-butenyl (2-trifluoromethylphenyl) carbonate, 2-butenyl (2-trifluoromethylphenyl) carbonate, 3-butenyl (2-trifluoromethylphenyl) carbonate, 2-pentenyl (2-trifluoromethylphenyl) carbonate, 2-hexenyl (2-trifluoromethylphenyl) carbonate, 2-propynyl (2-trifluoromethylphenyl) carbonate, 2-butynyl (2-trifluoromethylphenyl) carbonate, 3-butynyl (2-trifluoromethylphenyl) carbonate, 4-pentynyl (2-trifluoromethylphenyl) carbonate, 5-hexynyl (2-trifluoromethylphenyl) carbonate, 1-methyl-2-propynyl (2-trifluoromethylphenyl) carbonate, 1-methyl-2-butynyl (2-trifluoromethylphenyl) carbonate, 1,1-dimethyl-2-propynyl (2-trifluoromethylphenyl) carbonate, phenyl (2-trifluoromethylphenyl) carbonate, 2-methylphenyl (2-trifluoromethylphenyl) carbonate, 3-methylphenyl (2-trifluoromethylphenyl) carbonate, 4-methylphenyl (2-trifluoromethylphenyl) carbonate, 4-tert-butylphenyl (2-trifluoromethylphenyl) carbonate, 2,4,6-trimethylphenyl (2-trifluoromethylphenyl) carbonate, 2-fluorophenyl (2-trifluoromethylphenyl) carbonate, 3-fluorophenyl (2-trifluoromethylphenyl) carbonate, 4-fluorophenyl (2-trifluoromethylphenyl) carbonate, 2,4-difluorophenyl (2-trifluoromethylphenyl) carbonate, 2,6-difluorophenyl (2-trifluoromethylphenyl) carbonate, 3,4-difluorophenyl (2-trifluoromethylphenyl) carbonate, 2,4,6-trifluorophenyl (2-trifluoromethylphenyl) carbonate, pentafluorophenyl (2-trifluoromethylphenyl) carbonate, bis(2-trifluoromethylphenyl) carbonate, 3-trifluoromethylphenyl (2-trifluoromethylphenyl) carbonate, 4-trifluoromethylphenyl (2-trifluoromethylphenyl) carbonate, methyl (3-trifluoromethylphenyl) carbonate, ethyl (3-trifluoromethylphenyl) carbonate, vinyl (3-trifluoromethylphenyl) carbonate, 2-propynyl (3-trifluoromethylphenyl) carbonate, bis(3-trifluoromethylphenyl) carbonate, methyl (4-trifluoromethylphenyl) carbonate, ethyl (4-trifluoromethylphenyl) carbonate, vinyl (4-trifluoromethylphenyl) carbonate, 2-propynyl (4-trifluoromethylphenyl) carbonate, bis(4-trifluoromethylphenyl) carbonate, 3,5-bis(trifluoromethyl)phenyl methyl carbonate, 3,5-bis(trifluoromethyl)phenyl ethyl carbonate, 3,5-bis(trifluoromethyl)phenyl vinyl carbonate, 3,5-bis(trifluoromethyl)phenyl 2-propynyl carbonate, bis(3,5-bis(trifluoromethyl)phenyl) carbonate, 2,3-bis(trifluoromethyl)phenyl methyl carbonate, bis(2,3-bis(trifluoromethyl)phenyl) carbonate, 2,4-bis(trifluoromethyl)phenyl methyl carbonate, bis(2,4-bis(trifluoromethyl)phenyl) carbonate, 2,5-bis(trifluoromethyl)phenyl methyl carbonate, bis(2,5-bis(trifluoromethyl)phenyl) carbonate, 2,6-bis(trifluoromethyl)phenyl methyl carbonate, bis(2,6-bis(trifluoromethyl)phenyl) carbonate, 2,3,4-tris(trifluoromethyl)phenyl methyl carbonate, 2,3,5-tris(trifluoromethyl)phenyl methyl carbonate, 2,3,6-tris(trifluoromethyl)phenyl methyl carbonate, etc.

(ii) As the case where $Y^1$ is a sulfonyl group:

Preferably mentioned are 2-trifluoromethylphenyl methanesulfonate, 2-trifluoromethylphenyl ethanesulfonate, 2-trifluoromethylphenyl propane-1-sulfonate, 2-trifluoromethylphenyl butane-1-sulfonate, 2-trifluoromethylphenyl pentane-1-sulfonate, 2-trifluoromethylphenyl hexane-1-sulfonate, 2-trifluoromethylphenyl propane-2-sulfonate, 2-trifluoromethylphenyl butane-2-sulfonate, 2-trifluoromethylphenyl 2-methylpropane-2-sulfonate, 2-trifluoromethylphenyl 2-methylbutane-2-sulfonate, 2-trifluoromethylphenyl fluoromethanesulfonate, 2-trifluoromethylphenyl trifluoromethanesulfonate, 2-trifluoromethylphenyl 2,2,2-trifluoroethanesulfonate, 2-trifluoromethylphenyl benzenesulfonate, 2-trifluoromethylphenyl 2-methylbenzenesulfonate, 2-trifluoromethylphenyl 3-methylbenzenesulfonate, 2-trifluoromethylphenyl 4-methylbenzenesulfonate, 2-trifluoromethylphenyl 4-tert-butylbenzenesulfonate, 2-trifluoromethylphenyl 2,4,6-trimethylbenzenesulfonate, 2-trifluoromethylphenyl 2-fluorobenzenesulfonate, 2-trifluoromethylphenyl 3-fluorobenzenesulfonate, 2-trifluoromethylphenyl 4-fluorobenzenesulfonate, 2-trifluoromethylphenyl 2,4-difluorobenzenesulfonate, 2-trifluoromethylphenyl 2,6-difluorobenzenesulfonate, 2-trifluoromethylphenyl 3,4-difluorobenzenesulfonate, 2-trifluoromethylphenyl 2,4,6-trifluorobenzenesulfonate, 2-trifluoromethylphenyl pentafluorobenzenesulfonate, 2-trifluoromethylphenyl 2-trifluoromethylbenzenesulfonate, 3-trifluoromethylphenyl methanesulfonate, 3-trifluoromethylphenyl ethanesulfonate, 3-trifluoromethylphenyl benzenesulfonate, 3-trifluoromethylphenyl 4-methylbenzenesulfonate, 4-trifluoromethylphenyl methanesulfonate, 4-trifluoromethylphenyl ethanesulfonate, 4-trifluoromethylphenyl benzenesulfonate, 4-trifluoromethylphenyl 4-methylbenzenesulfonate, 3,5-bis(trifluoromethyl)phenyl methanesulfonate, 3,5-bis(trifluoromethyl)phenyl ethanesulfonate, 2,3-bis(trifluoromethyl)phenyl methanesulfonate, 2,3-bis(trifluoromethyl)phenyl ethanesulfonate, 2,4-bis(trifluoromethyl)phenyl methanesulfonate, 2,4-bis(trifluoromethyl)phenyl ethanesulfonate, 2,5-bis(trifluoromethyl)phenyl methanesulfonate, 2,5-bis(trifluoromethyl)phenyl ethanesulfonate, 2,6-bis(trifluoromethyl)phenyl methanesulfonate, 2,6-bis(trifluoromethyl)phenyl ethanesulfonate, 2,3,4-tris(trifluoromethyl)phenyl methanesulfonate, 2,3,5-tris(trifluoromethyl)phenyl methanesulfonate, 2,3,6-tris(trifluoromethyl)phenyl methanesulfonate, 2-(2,2,2-trifluoroethyl)phenyl methanesulfonate, 2-(perfluoroethyl)phenyl methanesulfonate, 2-(perfluoropropyl)phenyl methanesulfonate, 2-(perfluorobutyl)phenyl methanesulfonate, etc.

Of the halogenoalkylbenzene compounds of the above-mentioned (i) and (ii), more preferred are methyl (2-trifluoromethylphenyl) carbonate, ethyl (2-trifluoromethylphenyl) carbonate, n-propyl (2-trifluoromethylphenyl) carbonate, 2-propynyl (2-trifluoromethylphenyl) carbonate, 2-butynyl (2-trifluoromethylphenyl) carbonate, 3-butynyl (2-trifluoromethylphenyl) carbonate, phenyl (2-trifluoromethylphenyl) carbonate, 2-methylphenyl (2-trifluoromethylphenyl) carbonate, 3-methylphenyl (2-trifluoromethylphenyl) carbonate, 4-methylphenyl (2-trifluoromethylphenyl) carbonate, bis(2-trifluoromethylphenyl) carbonate, 2-trifluoromethylphenyl methanesulfonate, 2-trifluoromethylphenyl ethanesulfonate, 2-trifluoromethylphenyl benzenesulfonate, 2-trifluoromethylphenyl 2-methylbenzenesulfonate, 2-trifluoromethylphenyl 3-methylbenzenesulfonate, 2-trifluoromethylphenyl 4-methylbenzenesulfonate, 3-trifluoromethylphenyl methanesulfonate, 3-trifluoromethylphenyl ethanesulfonate, 3-trifluoromethylphenyl benzenesulfonate, 3-trifluoromethylphenyl 4-methylbenzenesulfonate, 4-trifluoromethylphenyl methanesulfonate, 4-trifluoromethylphenyl ethanesulfonate, 4-trifluoromethylphenyl benzenesulfonate, 4-trifluoromethylphenyl 4-methylbenzenesulfonate; and even more preferred are methyl (2-trifluoromethylphenyl) carbonate, ethyl (2-trifluoromethylphenyl) carbonate, 2-propynyl (2-trifluoromethylphenyl) carbonate, bis(2-trifluoromethylphenyl) carbonate 2-trifluoromethylphenyl methanesulfonate, 2-trifluoromethylphenyl ethanesulfonate, 2-trifluoromethylphenyl benzenesulfonate, 2-trifluoromethylphenyl 2-methylbenzenesulfonate, 2-trifluoromethylphenyl 3-methylbenzenesulfonate, 2-trifluoromethylphenyl 4-methylbenzenesulfonate.

In the nonaqueous electrolytic solution of the present invention, the content of the halogenoalkylbenzene compound represented by the above-mentioned general formula (I) is preferably from 0.001 to 10% by mass of the nonaqueous electrolytic solution. When the content is at most 10% by mass, then the risk of excessive formation of a surface film on the electrode to worsen the low-temperature characteristics of batteries could be low; and when at least 0.001% by mass, then the surface film formation would be sufficient and the effect of improving high-temperature storage characteristics could be enhanced. The content is more preferably at least 0.05% by mass of the nonaqueous electrolytic solution, even more preferably at least 0.2% by mass, and its upper limit is preferably at most 8% by mass, more preferably at most 5% by mass, even more preferably at most 2% by mass.

In the nonaqueous electrolytic solution of the present invention, combining the halogenoalkylbenzene compound represented by the above-mentioned general formula (I) with the nonaqueous solvent, electrolyte salt and other additives to be mentioned below exhibits a specific effect of synergistically improving the electrochemical characteristics of batteries in a broad temperature range.

[Nonaqueous Solvent]

The nonaqueous solvent for use in the nonaqueous electrolytic solution of the present invention includes cyclic carbonates, linear esters, lactones, ethers, amides, phosphates, sulfones, nitriles, isocyanates, S=O bond-containing compounds, etc. Preferably, the solvent contains both a cyclic carbonate and a linear ester.

The term "linear ester" is used here as a concept including linear carbonates and linear carboxylates.

As the cyclic carbonates, there may be mentioned ethylene carbonate (EC), propylene carbonate (PC), 1,2-butylene carbonate, 2,3-butylene carbonate, 4-fluoro-1,3-dioxolan-2-one (FEC), trans or cis-4,5-difluoro-1,3-dioxolan-2-one (hereinafter the two are collectively called "DFEC"), vinylene carbonate (VC), vinylethylene carbonate (VEC), etc.

Of those, preferred is use of at least one cyclic carbonate having a carbon-carbon double bond or a fluorine atom, as markedly enhancing low-temperature load characteristics after high-temperature charging storage; and more preferred is use of both a cyclic carbonate having a carbon-carbon double bond and a cyclic carbonate having a fluorine atom. As the cyclic carbonate having a carbon-carbon double bond, more preferred are VC and VEC; and as the cyclic carbonate having a fluorine atom, more preferred are FEC and DFEC.

The content of the carbon-carbon double bond-containing cyclic carbonate is preferably at least 0.07% by volume relative to the total volume of the nonaqueous solvent, more preferably at least 0.2% by volume, even more preferably at least 0.7% by volume, and the upper limit thereof is preferably at most 7% by volume, more preferably at most 4% by volume, even more preferably at most 2.5% by volume. Falling within the range, the stability of the surface film during high-temperature storage can be markedly enhanced not detracting from the low-temperature Li ion permeability thereof.

The content of the fluorine atom-containing cyclic carbonate is preferably at least 0.07% by volume relative to the total volume of the nonaqueous solvent, more preferably at least 4% by volume, even more preferably at least 7% by volume, and the upper limit thereof is preferably at most 35% by volume, more preferably at most 25% by volume, even more preferably at most 15% by volume. Falling within the range, the stability of the surface film during high-temperature storage can be markedly enhanced not detracting from the low-temperature Li ion permeability thereof.

In case where the nonaqueous solvent contains both a carbon-carbon double bond-containing cyclic carbonate and a fluorine atom-containing cyclic carbonate, the content of the carbon-carbon double bond-containing cyclic carbonate relative to the content of the fluorine atom-containing cyclic carbonate is preferably at least 0.2% by volume, more preferably at least 3% by volume, even more preferably at least 7% by volume, and its upper limit is preferably at most 40% by volume, more preferably at most 30% by volume, even more preferably at most 15% by volume. Falling within the range, the stability of the surface film during high-temperature storage can be markedly enhanced not detracting from the low-temperature Li ion permeability thereof.

Preferably, the nonaqueous solvent contains ethylene carbonate and/or propylene carbonate, as the resistance of the surface film formed on electrodes can be reduced. Preferably, the content of ethylene carbonate and/or propylene carbonate is at least 3% by volume relative to the total volume of the nonaqueous solvent, more preferably at least 5% by volume, even more preferably at least 7% by volume, and its upper limit is preferably at most 45% by volume, more preferably at most 35% by volume, even more preferably at most 25% by volume.

One kind of those solvents may be used, but using two or more different kinds thereof as combined is preferred as further enhancing the electrochemical characteristics in a broad temperature range. Even more preferably, three or more different kinds are combined. Preferred combinations of the cyclic carbonates include EC and PC; EC and VC; PC and VC; VC and FEC; EC and FEC; PC and FEC; FEC and DFEC; EC and DFEC; PC and DFEC; VC and DFEC; VEC and DFEC; EC and PC and VC; EC and PC and FEC; EC and VC and FEC; EC and VC and VEC; PC and VC and FEC; EC and VC and DFEC; PC and VC and DFEC; EC and PC and VC and FEC; EC and PC and VC and DFEC; etc. Of those combinations, more preferred combinations are EC and VC; EC and FEC; PC and FEC; EC and PC and VC; EC and PC and FEC; EC and VC and FEC; PC and VC and FEC; EC and PC and VC and FEC; etc.

As the linear esters, preferably mentioned are asymmetric linear carbonates, such as methyl ethyl carbonate (MEC), methyl propyl carbonate (MPC), methyl isopropyl carbonate (MIPC), methyl butyl carbonate, and ethyl propyl carbonate, etc.; symmetric linear carbonates, such as dimethyl carbonate (DMC), diethyl carbonate (DEC), dipropyl carbonate, dibutyl carbonate, etc.; pivalates, such as methyl pivalate, ethyl pivalate, propyl pivalate, etc.; linear carboxylates, such as methyl propionate, ethyl propionate, methyl acetate, ethyl acetate, etc.

Of the above-mentioned linear esters, preferred are methyl group-having linear esters selected from dimethyl carbonate, methyl ethyl carbonate, methyl propyl carbonate, methyl isopropyl carbonate, methyl butyl carbonate, methyl propionate, methyl acetate and ethyl acetate; and more preferred are methyl group-having linear carbonates.

Preferably, two or more different types of linear carbonates are used here. More preferably, a combination of a symmetric linear carbonate and an asymmetric linear carbonate is used; and even more preferably, the content of the symmetric linear carbonate is larger than that of the asymmetric linear carbonate.

Not specifically defined, the content of the linear ester is preferably within a range of from 60 to 90% by volume relative to the total volume of the nonaqueous solvent. When the content is at least 60% by volume, then the risk of increasing the viscosity of the nonaqueous electrolytic solution may be low; and when at most 90% by volume, then the risk of lowering the electric conductivity of the nonaqueous electrolytic solution to worsen the electrochemical characteristics in use thereof in a broad temperature range may be low. For these reasons, the above-mentioned range is preferred here.

The ratio by volume of the symmetric linear carbonate to the linear carbonate is preferably at least 51% by volume, more preferably at least 55% by volume, and its upper limit is preferably at most 95% by volume, more preferably at most 85% by volume. Especially preferably, the symmetric linear carbonate for use herein contains dimethyl carbonate. Also preferably, the asymmetric linear carbonate for use herein has a methyl group, and especially preferred is use of methyl ethyl carbonate here.

The above-mentioned embodiments are preferred as enhancing the electrochemical characteristics of batteries in a markedly broad range.

The ratio of the cyclic carbonate to the linear ester, cyclic carbonate/linear ester (by volume) is preferably from 10/90 to 45/55, more preferably from 15/85 to 40/60, even more preferably from 20/80 to 35/65, from the viewpoint of enhancing the electrochemical characteristics in a broad temperature range.

The lactones include γ-butyrolactone, γ-valerolactone, α-angelicalactone, etc.; the ethers include cyclic ethers, such as tetrahydrofuran, 2-methyltetrahydrofuran, 1,3-dioxolane, 1,3-dioxane, 1,4-dioxane, etc., and linear ethers, such as 1,2-dimethoxyethane, 1,2-diethoxyethane, 1,2-dibutoxyethane, etc.

The amides include dimethylformamide, etc.; the phosphates include trimethyl phosphate, tributyl phosphate, trioctyl phosphate, etc.; the sulfones include sulfolane, etc.; the nitriles include acetonitrile, propionitrile, succinonitrile, glutaronitrile, adiponitrile, pimelonitrile, etc.; and the isocyanates include tetramethylene diisocyanate, hexamethylene diisocyanate, octamethylene diisocyanate, etc.

The S=O bond-containing compounds include sultone compounds, such as 1,3-propanesultone, 1,3-butanesultone, 2,4-butanesultone, 1,4-butanesultone, etc.; cyclic sulfite compounds, such as ethylene sulfite, hexahydrobenzo[1,3,2]dioxathiolane-2-oxide (also referred to as 1,2-cyclohexanediol cyclic sulfite), 5-vinyl-hexahydro-1,3,2-benzo-dioxathiol-2-oxide, etc.; sulfonic acid ester compounds, such as 2-propynyl methanesulfonate, methylenemethane disulfonate, etc.; and vinyl sulfone compounds, such as divinyl sulfone, 1,2-bis(vinylsulfonyl)ethane, bis(2-vinylsulfonylethyl) ether, etc.

As other nonaqueous solvents, preferably used here are oxalates, such as dimethyl oxalate, ethylmethyl oxalate, diethyl oxalate, etc.; linear carboxylic acid anhydrides, such as acetic anhydride, propionic anhydride, etc.; cyclic acid anhydrides, such as succinic anhydride, maleic anhydride, glutaric anhydride, itaconic anhydride, 3-sulfo-propionic anhydride, etc.; cyclic phosphazene compounds, such as methoxypentafluorocyclotriphosphazene, ethoxypentafluorocyclotriphosphazene, phenoxypentafluorocyclotriphosphazene, ethoxyheptafluorocyclotetraphosphazene, etc.; branched alkyl group-having aromatic compounds, such as cyclohexylbenzene, fluorocyclohexylbenzene compounds (including 1-fluoro-2-cyclohexylbenzene, 1-fluoro-3-cyclohexylbenzene, and 1-fluoro-4-cyclohexylbenzene), tert-butylbenzene, tert-amylbenzene, 1-fluoro-4-tert-butylbenzene, etc.; and other aromatic compounds, such as biphenyl, terphenyls (o-, m-, and p-form), diphenyl ether, fluorobenzene, difluorobenzenes (o-, m-, and p-form), anisole, 2,4-difluoroanisole, partially hydrogenated terphenyls (including 1,2-dicyclohexylbenzene, 2-phenylbicyclohexyl, 1,2-diphenylcyclohexane, and o-cyclohexylbiphenyl), etc.

In general, the above-mentioned nonaqueous solvents are combined and used as a mixture thereof for attaining suitable physical properties. Preferred combinations include, for example, a combination of a cyclic carbonate and a linear carbonate, a combination of a cyclic carbonate and a linear carboxylate, a combination of a cyclic carbonate, a linear carbonate and a lactone, a combination of a cyclic carbonate, a linear carbonate and an ether, a combination of a cyclic carbonate, a linear carbonate and a linear carboxylate, etc.

[Electrolyte Salt]

As the electrolyte salt for use in the present invention, preferably mentioned are the following lithium salts and onium salts.

(Lithium Salt)

The lithium salt includes inorganic lithium salts, such as $LiPF_6$, $LiPO_2F_2$, $Li_2PO_3F$, $LiBF_4$, $LiClO_4$, etc.; linear fluoroalkyl group-having lithium salts, such as $LiN(SO_2CF_3)_2$, $LiN(SO_2C_2F_0)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_6(iso-C_3F_7)$, etc.; cyclic fluoroalkylene chain-having lithium salts, such as $(CF_2)_2(SO_2)_2NLi$, $(CF_2)_3(SO_2)_2NLi$, etc.; and lithium salts with an oxalate complex as the anion therein, such as lithium bis[oxalate-O,O']borate, lithium difluoro[oxalate-O,O']borate, etc. One or more of these as compound may be used here.

Of those, preferred is at least one selected from $LiPF_6$, $LiPO_2F_2$, $Li_2PO_3F$, $LiBF_4$, $LiN(SO_2CF_3)_2$ and $LiN(SO_2C_2F_6)_2$; and more preferred is at least one selected from $LiPF_6$, $LiPO_2F_2$, $LiBF_4$ and $LiN(SO_2CF_3)_2$.

The concentration of the lithium salt is preferably at least 0.3 M relative to the above-mentioned nonaqueous solvent, more preferably at least 0.7 M, even more preferably at least 1.1 M. The upper limit of the content is preferably at most 2.5 M, more preferably at most 2.0 M, even more preferably at most 1.6 M.

A preferred combination of these lithium salts to be contained in the nonaqueous electrolytic solution comprises $LiPF_6$ and contains at least one lithium salt selected from $LiPO_2F_2$, $LiBF_4$ and $LiN(SO_2CF_3)_2$.

When the proportion of the lithium salt except $LiPF_6$ to be in the nonaqueous solvent is at least 0.001 M, then the electrolytic solution could readily exhibit the effect thereof of enhancing the electrochemical characteristics at high temperature, and when the content is at most 0.005 M, then the risk of depressing the effect of enhancing the electrochemical characteristics at high temperature would be low, and the range is therefore preferred. Preferably, the proportion of the lithium salt except $LiPF_6$ in the nonaqueous solvent is at least 0.01 M, more preferably at least 0.03 M, most preferably at least 0.04 M. The upper limit of the proportion is preferably at most 0.4 M, more preferably at most 0.2 M.

(Onium Salt)

Preferred examples of the onium salt are various salts of a combination of an onium cation and an anion mentioned below.

As the onium cation, preferably mentioned are a tetramethylammonium cation, an ethyltrimethylammonium cation, a diethyldimethylammonium cation, a triethylmethylammonium cation, a tetraethylammonium cation, an N,N-dimethylpyrrolidinium cation, an N-ethyl-N-methylpyrrolidinium cation, an N,N-diethylpyrrolidinium cation, a spiro-(N,N')-bipyrrolidinium cation, an N,N'-dimethylimidazolinium cation, an N-ethyl-N'-methylimidazolinium cation, an N,N'-diethylimidazolinium cation, an N,N'-dimethylimidazolinium cation, an N-ethyl-N'-methylimidazolinium cation, an N,N'-diethylimidazolinium cation, etc.

Preferred examples of the anion include a $PF_6$ anion, a $BF_4$ anion, a $ClO_4$ anion, an $AsF_6$ anion, a $CF_3SO_3$ anion, an $N(CF_3SO_2)_2$ anion, an $N(C_2F_5SO_2)_2$ anion, etc.

One alone or two or more different types of these electrolyte salts may be used here either singly or as combined.

[Production of Nonaqueous Electrolytic Solution]

The nonaqueous electrolytic solution of the present invention may be produced, for example, by mixing the above-mentioned nonaqueous solvents, adding the above-mentioned electrolyte salt, and further adding thereto the halogenoalkylbenzene compound represented by the above-mentioned general formula (I) to the resulting nonaqueous electrolytic solution.

Preferably, the nonaqueous solvent to be used and the compound to be added to the nonaqueous electrolytic solution are previously purified to reduce as much as possible the content of impurities therein within a range not extremely detracting from the productivity.

The nonaqueous electrolytic solution of the present invention can be used in the first to fourth energy storage devices mentioned below, in which as the nonaqueous electrolyte, not only a liquid one but also a gelled one may be used. Further, the nonaqueous electrolytic solution of the present invention can also be used for solid polymer electrolytes. Especially preferably, the solution is used in the first energy storage device where a lithium salt is used as the electrolyte salt (that is, for lithium batteries), or in the fourth energy storage device (that is, for lithium ion capacitors); and more suitably, the solution is used for lithium batteries, even more preferably for lithium secondary batteries.

[First Energy Storage Device (Lithium Battery)]

The lithium battery in this specification means a generic name for a lithium primary battery and a lithium secondary battery. In this specification, the term, lithium secondary battery is used as a concept that includes so-called lithium ion secondary batteries. The lithium battery of the present invention comprises a positive electrode, a negative electrode, and the above-mentioned nonaqueous electrolytic solution of an electrolyte salt dissolved in a nonaqueous solvent. The other constitutive members, such as the positive electrode, the negative electrode and others than the nonaqueous electrolytic solution are not specifically defined for use herein.

For example, as the positive electrode active material for lithium secondary batteries, usable is a complex metal oxide of lithium and one or more selected from cobalt, manganese and nickel. One alone or two or more of these positive electrode active materials may be used here either singly or as combined.

The lithium complex metal oxide includes, for example, $LiCoO_2$, $LiMn_2O_4$, $LiNiO_2$, $LiCo_{1-x}Ni_xO_2(0.01<x<1)$, $LiCo_{1/3}Ni_{1/3}Mn_{1/3}O_2$, $LiNi_{1/2}Mn_{3/2}O_4$, $LiCo_{0.98}Mg_{0.02}O_2$, etc. Also usable here is a combination of $LiCoO_2$ and $LiMn_2O_4$, a combination of $LiCoO_2$ and $LiNiO_2$, or a combination of $LiMn_2O_4$ and $LiNiO_2$.

For improving the safety in overcharging and the cycle properties of the batteries, or for enabling the use thereof at a charge potential of 4.3 V or more, a part of the lithium complex metal oxide may be substituted with any other element. For example, a part of cobalt, manganese and nickel may be substituted with at least one or more elements of Sn, Mg, Fe, Ti, Al, Zr, Cr, V, Ga, Zn, Cu, Bi, Mo, La, etc.; or a part of O may be substituted with S or F; or the oxide may be coated with a compound containing any of such other elements.

Of those, preferred are lithium complex metal oxides, such as $LiCoO_2$, $LiMn_2O_4$ and $LiNiO_2$, with which the charge potential of the positive electrode in a fully-charged state could be 4.3 V or more based on Li; and more preferred are lithium complex metal oxides, such as solid solutions of $LiCo_{1-x}M_xO_2$ (where M is one or more elements selected from Sn, Mg, Fe, Ti, Al, Zr, Cr, V, Ga, Zn and Cu; $0.001 \leq x \leq 0.05$), $LiCo_{1/3}Ni_{1/3}Mn_{1/3}O_2$, $LiNi_{1/2}Mn_{3/2}O_4$, $Li_2MnO_3$ and $LiMO_2$ (where M is a transition metal, such as Co, Ni, Mn, Fe, etc.) that can be used at 4.4 V or more. When the lithium complex metal oxide capable of acting at a high charge voltage is used, then the electrochemical characteristics in use thereof in an especially broad temperature range may often worsen owing to the reaction of the oxide with the electrolytic solution in charging; however, in the lithium secondary battery of the present invention, the electrochemical characteristics can be prevented from worsening.

In particular, a battery with an Mn-containing positive electrode tends to have an increased resistance owing to the release of Mn ion from the positive electrode, and therefore in use in a broad temperature range, the electrochemical characteristics of the battery of the type tends to worsen. However, of the lithium secondary battery of the present invention, the electrochemical characteristics can be prevented from worsening and the battery is therefore preferred.

Further, lithium-containing olivine-type phosphates are also usable as the positive electrode active material. Especially preferred are lithium-containing olivine-type phosphates containing at least one or more selected from iron, cobalt, nickel and manganese. As their specific examples, there may be mentioned $LiFePO_4$, $LiCoPO_4$, $LiNiPO_4$, $LiMnPO_4$, etc.

The lithium-containing olivine-type phosphates may be partly substituted with any other element. For example, a part of iron, cobalt, nickel and manganese therein may be substituted with one or more elements selected from Co, Mn, Ni, Mg, Al, B, Ti, V, Nb, Cu, Zn, Mo, Ca, Sr, W and Zr; or the phosphates may be coated with a compound containing any of these other elements or with a carbon material. Of those, preferred are $LiFePO_4$ and $LiMnPO_4$.

The lithium-containing olivine-type phosphate may be combined with, for example, the above-mentioned positive electrode active material.

For the positive electrode for lithium primary batteries, there are mentioned oxides or chalcogen compounds of one or more metal elements, such as CuO, $Cu_2O$, $Ag_2O$, $Ag_2CrO_4$, CuS, $CuSO_4$, $TiO_2$, $TiS_2$, $SiO_2$, SnO, $V_2O_5$, $V_6O_{12}$, $VO_x$, $Nb_2O_5$, $Bi_2O_3$, $Bi_2Pb_2O_5$, $Sb_2O_3$, $Cr_2O_3$, $Cr_2O_3$, $MoO_3$, $WO_3$, $SeO_2$, $MnO_2$, $Mn_2O_3$, $Fe_2O_3$, FeO, $Fe_3O_4$, $Ni_2O_3$, NiO, $CoO_3$, CoO, etc.; sulfur compounds, such as $SO_2$, $SOCl_2$, etc.; carbon fluorides (graphite fluoride) represented by a general formula $(CF_x)_n$, etc. Of those, preferred are $MnO_2$, $V_2O_5$, fluorographite, etc.

Not specifically defined, the electroconductive agent of the positive electrode may be any electron-conductive material not undergoing chemical change. For example, it includes graphites, such as natural graphite (flaky graphite, etc.), artificial graphite, etc.; and carbon blacks, such as acetylene black, Ketjen black, channel black, furnace black, lamp black, thermal black, etc. Graphites and carbon blacks may be combined suitably. The amount of the electroconductive agent to be added to the positive electrode mixture is preferably from 1 to 10% by mass, more preferably from 2 to 5% by mass.

The positive electrode may be formed by mixing the above-mentioned positive electrode active material with an electroconductive agent, such as acetylene black, carbon black or the like, and with a binder, such as polytetrafluoroethylene (PTFE), polyvinylidene fluoride (PVDF), styrene/butadiene copolymer (SBR), acrylonitrile/butadiene copolymer (NBR), carboxymethyl cellulose (CMC), ethylene/propylene/diene terpolymer or the like, then adding thereto a high-boiling point solvent, such as 1-methyl-2-pyrrolidone or the like, and kneading them to give a positive electrode mixture, thereafter applying the positive electrode mixture onto an aluminium foil or a stainless lath plate or the like serving as a collector, and drying and shaping it under pressure, and then heat-treating it in vacuum at a temperature of from 50° C. to 250° C. or so for about 2 hours.

The density of the part except the collector of the positive electrode may be generally at least 1.5 $g/cm^3$, and for further increasing the capacity of the battery, the density is preferably at least 2 $g/cm^3$, more preferably at least 3 $g/cm^3$, even more preferably at least 3.6 $g/cm^3$. The upper limit is preferably at most 4 $g/cm^3$.

As the negative electrode active material for the lithium secondary battery, usable are one or more of lithium metal, lithium alloys, carbon materials capable of absorbing and releasing lithium [graphatizable carbon, non-graphatizable carbon where the lattice (002) spacing is at least 0.37 nm, graphite where the lattice (002) spacing is at most 0.34 nm, etc.], tin (elementary substance), tin compounds, silicon (elementary substance), silicon compounds, lithium titanate compounds, such as $Li_4Ti_5O_{12}$ and the like, either singly or as combined with two or more thereof.

Of those, more preferred is use of high-crystalline carbon materials, such as artificial graphite, natural graphite and the like, in view of the ability thereof to absorb and release lithium ions, and even more preferred is use of a carbon material having a graphite-type crystal structure where the lattice (002) spacing ($d_{002}$) is at most 0.340 nm (nanometers), especially from 0.335 to 0.337 nm.

In particular, preferred here is use of artificial graphite particles having a bulky structure where plural flattened graphite fine particles aggregate or bond together non-parallel to each other, or graphite particles produced through treatment of spheroidization of flaky natural graphite particles by imparting thereto repeated mechanical action, such as compression force, friction force, shear force or the like. Preferably, the ratio of the peak intensity I (110) of the (110) plane of the graphite crystal obtained in X-ray diffractometry of a negative electrode sheet as formed by pressing so that the density of the part except the collector of the negative electrode could be at least 1.5 $g/cm^3$, to the peak intensity I (004) of the (004) plane thereof, I(110)/I(004) is at least 0.01, since the electrochemical characteristics of the battery can be enhanced in a markedly broad temperature range. More preferably, the ratio is at least 0.05, even more preferably at least 0.1. On the other hand, when too much processed, then the crystallinity may worsen and the discharge capacity of the battery may lower; and therefore, the upper limit of the peak intensity I(110)/I(004) is preferably at most 0.5, more preferably at most 0.3.

Preferably, the high-crystalline carbon material (core material) is coated with a different carbon material that is more low-crystalline than the core material, as further bettering the electrochemical characteristics in a broad temperature range. The crystallinity of the carbon material in coating may be confirmed through TEM.

When the high-crystalline carbon material is used, it may readily react with the nonaqueous electrolytic solution in charging to thereby worsen the electrochemical characteristics at low temperature or at high temperature owing to the increase in the interfacial resistance; however, in the lithium secondary battery of the present invention, the electrochemical characteristics in a broad range can be improved.

The metal compound capable of absorbing and releasing lithium, serving as a negative electrode active material, includes compounds containing at least one metal element of Si, Ge, Sn, Pb, P, Sb, Bi, Al, Ga, In, Ti, Mn, Fe, Co, Ni, Cu, Zn, Ag, Mg, Sr, Ba, etc. These metal compounds may have any morphology of elementary substances, alloys, oxides, nitrides, sulfides, borides, alloys with lithium or the like; but preferred are any of elementary substances, alloys, oxides and alloys with lithium, as capable of increasing the battery capacity. Above all, more preferred are those containing at least one element selected from Si, Ge and Sn, and even more preferred are those containing at least one element selected from Si and Sn, as capable of increasing the battery capacity.

The negative electrode may be formed, using the same electroconductive agent, binder and high-boiling point solvent as in the formation of the above-mentioned positive electrode. These are mixed and kneaded to give a negative electrode mixture, then the negative electrode mixture is applied onto a copper foil or the like serving as a collector, then dried and shaped under pressure, and thereafter heat-treated in vacuum at a temperature of from 50° C. to 250° C. or so for about 2 hours.

The density of the part except the collector of the negative electrode may be generally at least 1.1 $g/cm^3$, and for further increasing the battery capacity, the density is preferably at least 1.5 $g/cm^3$, more preferably at least 1.7 $g/cm^3$. The upper limit is preferably at most 2 $g/cm^3$.

As the negative electrode active material for lithium primary batteries, usable are lithium metal or lithium alloys.

The structure of the lithium battery is not specifically defined. The battery may be a coin-type battery, a cylinder-type battery, a square-shaped battery, a laminate-type battery or the like, each having a single-layered or multi-layered separator.

The separator for the battery is not specifically defined, for which usable is a single-layer or laminate porous film of polyolefin, such as polypropylene, polyethylene or the like, as well as a woven fabric, a nonwoven fabric, etc.

The lithium secondary battery of the present invention has excellent electrochemical characteristics in a broad temperature range even when the final charging voltage is 4.2 V or more, especially 4.3 V or more, and further, the electrochemical characteristics of the battery are still good even at 4.4 V or more. The final discharging voltage could be generally 2.8 V or more, further 2.5 V or more; however, the discharging final voltage of the lithium secondary battery of the present invention could be 2.0 V or more. The current value is not specifically defined, but in general, the battery is used within a range of from 0.1 to 30 C. The lithium battery of the present invention can be charged/discharged at −40 to 100° C., preferably at −10 to 80° C.

In the present invention, as a countermeasure against the increase in the internal pressure of the lithium battery, there may be employed a method of providing a safety valve in the battery cap or a method of forming a cutout in the battery component, such as the battery can, the gasket or the like. In addition, as a safety countermeasure against overcharging, a current cut-off mechanism capable of detecting the internal pressure of the battery to cut off the current may be provided in the battery cap.

[Second Energy Storage Device (Electric Double-Layer Capacitor)]

This is an energy storage devices that stores energy by utilizing the electric double layer capacitance in the interface between the electrolytic solution and the electrode therein. One example of the present invention is an electric double layer capacitor. The most typical electrode active material to be used in the energy storage device is active carbon. The double layer capacitance increases almost in proportion to the surface area.

[Third Energy Storage Device]

This is an energy storage device that stores energy by utilizing the doping/dedoping reaction of the electrode therein. As the electrode active material for use in the energy storage device, there may be mentioned metal oxides, such as ruthenium oxide, iridium oxide, tungsten oxide, molybdenum oxide, copper oxide, etc.; n-conjugated polymers, such as polyacene, polythiophene derivatives, etc. The capacitor that uses the electrode active material of the type enables energy storage along with the doping/dedoping reaction at the electrode therein.

[Fourth Energy Storage Device (Lithium Ion Capacitor)]

This is an energy storage device that stores energy by utilizing the lithium ion intercalation into the carbon material, such as graphite or the like of the negative electrode therein. This may be referred to as a lithium ion capacitor (LIC). As the positive electrode, for example, there may be mentioned one that utilizes the electric double layer between the active carbon electrode and the electrolytic solution therein, or one that utilizes the doping/dedoping reaction of the π-conjugated polymer electrode therein. The electrolytic solution contains at least a lithium salt, such as $LiPF_6$ or the like.

The trifluoromethylbenzene compound of the present invention is represented by the following general formula (II):

[Chem. 4]

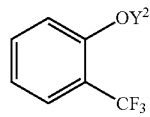

(II)

(In the formula, $Y^2$ represents a linear alkoxycarbonyl group having from 2 to 8 carbon atoms, an alkenyloxycarbonyl group having from 3 to 9 carbon atoms, an alkynyloxycarbonyl group having from 4 to 9 carbon atoms, an aryloxycarbonyl group having from 7 to 12 carbon atoms, an alkanesulfonyl group having from 1 to 6 carbon atoms, or an arylsulfonyl group having from 6 to 12 carbon atoms. In the substituent represented by $Y^2$, at least one hydrogen atom may be substituted with a halogen atom.)

Specific examples and preferred examples of the compound represented by the general formula (II) are the same as those described with respect to the general formula (I), and especially preferred compounds are methyl (2-trifluoromethylphenyl) carbonate, ethyl (2-trifluoromethylphenyl) carbonate, 2-propynyl (2-trifluoromethylphenyl) carbonate, bis(2-trifluoromethylphenyl) carbonate, 2-trifluoromethylphenyl methanesulfonate, 2-trifluoromethylphenyl ethanesulfonate, 2-trifluoromethylphenyl benzenesulfonate, and 2-trifluoromethylphenyl 4-methylbenzenesulfonate.

The compound represented by the general formula (II) can be produced according to the following methods, to which, however, the compound production is not limited.

(a) As the production method for the case where $Y^2$ is an alkoxycarbonyl group, an alkenyloxycarbonyl group, an alkynyloxycarbonyl group or an aryloxycarbonyl group, there may be mentioned a method of reacting a phenol compound with a corresponding haloformate in or not in a solvent and in the presence or absence of a base.

(b) As the production method for the case where $Y^2$ is an alkanesulfonyl group or an arylsulfonyl group, there may be mentioned a method of reacting a phenol compound with an alkanesulfonyl halide or an arylsulfonyl halide in or not in a solvent and in the presence or absence of a base.

In the above-mentioned (a) and (b), the amount of the haloformate, the alkanesulfonyl halide or the arylsulfonyl halide to be reacted with the phenol compound is preferably from 0.8 to 10 mols, more preferably from 1 to 5 mols, even more preferably from 1 to 3 mols relative to 1 mol of the diphenol compound.

Not specifically defined, the solvent to be used for the synthesis may be any one inert to the reaction. The usable solvent includes aliphatic hydrocarbons, halogenohydrocarbons, aromatic hydrocarbons, halogenoaromatic hydrocarbons, ethers, esters, carbonates, etc. Of those, especially preferred are aromatic hydrocarbons, such as toluene, xylene, etc.; esters, such as ethyl acetate, butyl acetate, etc.; carbonates, such as dimethyl carbonate, etc. The amount of the solvent to be used is preferably from 0 to 30 parts by mass, more preferably from 1 to 15 parts by mass relative to 1 part by mass of the phenol compound.

As the base, any of an inorganic base or an organic base is employable here. These may be used alone or as combined. The inorganic base usable here includes potassium carbonate, sodium carbonate, calcium hydroxide and calcium oxide. The organic base usable here includes aliphatic tertiary amines, and unsubstituted or substituted imidazoles, pyridines and pyrimidines. Especially preferred are trialkylamines, such as trimethylamine, triethylamine, tripropylamine, tributylamine, diisopropylethylamine, etc.; and pyridines, such as pyridine, N,N-dimethylaminopyridine, etc. The amount of the base to be used is preferably from 0.8 to 10 mols, more preferably from 1 to 5 mols, even more preferably from 1 to 5 mols relative to 1 mol of the phenol compound.

For the reaction, the lower limit of the reaction temperature is preferably not lower than −30° C., more preferably not lower than −10° C. from the viewpoint of not lowering the reactivity. The upper limit of the reaction temperature is preferably not higher than 100° C., more preferably not higher than 80° C. from the viewpoint of preventing side reaction and product decomposition.

The reaction time may be suitably changed depending on the reaction temperature and the reaction scale, but when the reaction time is too short, then unreacted matters would remain, and on the contrary, when the reaction time is too long, then the reaction product would decompose or side reaction would occur. Consequently, the reaction time is preferably from 0.1 to 24 hours, more preferably from 0.5 to 12 hours.

EXAMPLES

Synthesis Examples of the compound represented by the general formula (II) of the present invention, and Examples of electrolytic solutions are shown below; however, the present invention is not limited to these Examples.

Synthesis Example 1

Synthesis of ethyl (2-trifluoromethylphenyl)carbonate 3.00 g (18.5 mmol) of o-trifluoromethylphenol and 2.21 g (20.4 mmol) of ethyl chloroformate were dissolved in 40 ml of ethyl acetate, and 2.25 g (22.2 mmol) of triethylamine was dropwise added to the solution at an inner temperature of from 5 to 10° C., taking 20 minutes. After stirred for 1 hour at room temperature, the reaction liquid was washed three times with 20 ml of water to separate the organic layer, and the solvent was evaporated away under reduced pressure. The concentrate was purified through silica gel column chromatography (hexane/ethyl acetate=9/1 for elution) to give 3.94 g (yield 91%) of ethyl (2-trifluoromethylphenyl) carbonate.

The obtained ethyl (2-trifluoromethylphenyl) carbonate was analyzed through $^1$H-NMR (instrument: JEOL's "AL300") and mass spectrometry (instrument: Shimadzu's "GC-MS QP 2010 Ultra") to confirm the structure thereof. The results are shown below.

(1) $^1$H-NMR (300 MHz, CDCl$_3$): δ=7.69-7.31 (m, 4H), 4.34 (q, J=7.08 Hz, 2H), 1.39 (t, J=7.08 Hz, 3H)

(2) MS (EI): m/z (%)=189(4), 162(54), 142(100), 114(35)

Synthesis Example 2

Synthesis of 2-trifluoromethylphenyl methanesulfonate 3.00 g (18.5 mmol) of o-trifluoromethylphenol and 2.34 g (20.4 mmol) of methanesulfonyl chloride were dissolved in ml of ethyl acetate, and 2.34 g (20.4 mmol) of methanesulfonyl chloride was dropwise added to the solution at an inner temperature of from 5 to 10° C., taking 20 minutes. After stirred for 1 hour at room temperature, the reaction liquid was washed three times with 20 ml of water to separate the organic layer, and the solvent was evaporated away under reduced pressure. The concentrate was purified through silica gel column chromatography (hexane/ethyl acetate=3/1 for elution) to give 4.10 g (yield 93%) of 2-trifluoromethylphenyl methanesulfonate.

The obtained 2-trifluoromethylphenyl methanesulfonate was analyzed through $^1$H-NMR and mass spectrometry to confirm the structure thereof. The results are shown below.

(1) $^1$H-NMR (300 MHz, CDCl$_3$): δ=7.72-7.33 (m, 4H), 3.24 (s, 3H)

(2) MS (EI): m/z (%)=240(48) [M$^+$], 162(55), 142(100), 133(34), 114(30), 79(20)

Synthesis Example 3

Synthesis of 2-trifluoromethylphenyl 4-methylbenzenesulfonate

2-Trifluoromethylphenyl 4-methylbenzenesulfonate was synthesized according to the same method as in Synthesis Example 2. The results of $^1$H-NMR and MS of 2-trifluoromethylphenyl 4-methylbenzenesulfonate are shown below.

(1) $^1$H-NMR (300 MHz, CDCl$_3$): δ=7.86-7.32 (m, 8H), 2.46 (s, 3H)

(2) MS (EI): m/z (%)=316 (24) [M$^+$], 155 (92), 91(100)

Examples 1 to 15, Comparative Examples 1 to 3

Production of Lithium Ion Secondary Battery

94% by mass of LiCoO$_2$ and 3% by mass of acetylene black (electroconductive agent) were mixed, and added to and mixed in a solution previously prepared by dissolving 3% by mass of polyvinylidene fluoride (binder) in 1-methyl-2-pyrrolidone, thereby preparing a positive electrode mixture paste. The positive electrode mixture paste was applied on one surface of an aluminium foil (collector), then dried, processed under pressure and blanked into a predetermined size, thereby producing a positive electrode sheet. The density of the part of the positive electrode except the collector was 3.6 g/cm$^3$. On the other hand, 95% by mass of artificial graphite (d$_{002}$=0.335 nm, negative electrode active material) was added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto one surface of a copper foil (collector), dried, processed under pressure and blanked into a predetermined size, thereby producing a negative electrode sheet. The density of the part of the negative electrode except the collector was 1.5 g/cm$^3$. The electrode sheet was analyzed through X-ray diffractometry, and the ratio of the peak intensity I (110) of the (110) plane of the graphite crystal to the peak intensity I(004) of the (004) plane thereof [I(110)/I(004)] was 0.1. The positive electrode sheet, a porous polyethylene film separator and the negative electrode sheet were laminated in that order, and the nonaqueous electrolytic solution having the composition shown in Table 1 and 2 was added thereto to produce a 2032 coin-type battery.

[Evaluation of Low-Temperature Characteristics after High-Temperature Charging Storage]
<Initial Discharge Capacity>

In a thermostatic chamber kept at 25° C., the coin-type battery produced according to the above-mentioned method was charged up to a final voltage of 4.2 V for 3 hours with a constant current of 1 C and under a constant voltage, then the temperature of the thermostatic chamber was lowered to 0° C., and the battery was discharged under a constant current of 1 C to a final voltage of 2.75 V. The initial discharge capacity at 0° C. was measured.

<High-Temperature Charging Storage Test>

Next, in a thermostatic chamber at 85° C., the coin-type battery was charged up to a final voltage of 4.2 V for 3 hours with a constant current of 1 C and under a constant voltage, and then stored for 3 days while kept at 4.2 V. Subsequently, this was put in a thermostatic chamber at 25° C., and once discharged under a constant current of 1 C to a final voltage of 2.75 V.

<Discharge Capacity after High-Temperature Charging Storage>

Further after that, the discharge capacity at 0° C. after high-temperature charging storage was measured in the same manner as that for the measurement of the initial discharge capacity.

<Low-Temperature Characteristics after High-Temperature Charging Storage>

The low-temperature characteristics after high-temperature charging storage were determined based on the 0° C. discharge capacity retention rate mentioned below.

0° C. Discharge Capacity Retention Rate after high-temperature charging storage (%)=(discharge capacity at 0° C. after high-temperature charging storage/initial discharge capacity at 0° C.)× 100.

The battery production condition and the battery characteristics are shown in Tables 1 and 2.

TABLE 1

| | Composition of Electrolyte Salt Composition of Nonaqueous Electrolyte solution (ratio by volume of solvents) | Compound | | Amount Added (content in nonaqueous electrolytic solution) (wt %) | 0° C. Discharge Capacity Retention Rate after 85° C. high-temperature charging storage (%) |
|---|---|---|---|---|---|
| Example 1 | 1.2M LiPF6 EC/DMC/MEC (30/50/20) | [2-(trifluoromethyl)phenyl methanesulfonate structure] | 2-trifluoromethylphenyl methanesulfonate | 1 | 72 |
| Example 2 | 1.2M LiPF6 + 0.05M LiBF4 EC/VC/DMC/MEC (29/1/50/20) | [2-(trifluoromethyl)phenyl methanesulfonate structure] | 2-trifluoromethylphenyl methanesulfonate | 0.1 | 70 |
| Example 3 | 1.2M LiPF6 + 0.05M LiBF4 EC/VC/DMC/MEC (29/1/50/20) | [2-(trifluoromethyl)phenyl methanesulfonate structure] | 2-trifluoromethylphenyl methanesulfonate | 1 | 82 |
| Example 4 | 1.2M LiPF6 + 0.05M LiBF4 EC/VC/DMC/MEC (29/1/50/20) | [2-(trifluoromethyl)phenyl methanesulfonate structure] | 2-trifluoromethylphenyl methanesulfonate | 3 | 78 |
| Example 5 | 1.2M LiPF6 + 0.05M LiBF4 EC/VC/DMC/MEC (29/1/50/20) | [2-(trifluoromethyl)phenyl methanesulfonate structure] | 2-trifluoromethylphenyl methanesulfonate | 7 | 75 |
| Example 6 | 1.2M LiPF6 + 0.05M LiBF4 EC/VC/DMC/MEC (29/1/50/20) | [3-(trifluoromethyl)phenyl methanesulfonate structure] | 4-trifluoromethylphenyl methanesulfonate | 1 | 75 |
| Example 7 | 1.2M LiPF6 + 0.05M LiBF4 EC/VC/DMC/MEC (29/1/50/20) | [4-(trifluoromethyl)phenyl methanesulfonate structure] | 4-trifluoromethylphenyl methanesulfonate | 1 | 78 |

TABLE 1-continued

| | Composition of Electrolyte Salt Composition of Nonaqueous Electrolyte solution (ratio by volume of solvents) | Compound | | Amount Added (content in nonaqueous electrolytic solution) (wt %) | 0° C. Discharge Capacity Retention Rate after 85° C. high-temperature charging storage (%) |
|---|---|---|---|---|---|
| Example 8 | 1.2M LiPF6 + 0.05M LiBF4 EC/VC/DMC/MEC (29/1/50/20) | | 3,5-bis(trifluoromethyl)phenyl methanesulfonate | 1 | 83 |
| Example 9 | 1.2M LiPF6 + 0.05M LiBF4 EC/VC/DMC/MEC (29/1/50/20) | | 2-trifluoromethylphenyl 4-methylbenzenesulfonate | 1 | 76 |
| Example 10 | 1.2M LiPF6 + 0.05M LiBF4 EC/FEC/VC/DMC/MEC (24/5/1/50/20) | | 2-trifluoromethylphenyl methanesulfonate | 1 | 87 |
| Comparative Example 1 | 1.2M LiPF6 + 0.05M LiBF4 EC/VC/DMC/MEC (29/1/50/20) | — | — | — | 64 |

TABLE 2

| | Composition of Electrolyte Salt Composition of Nonaqueous Electrolyte solution (ratio by volume of solvents) | Compound | | Amount Added (content in nonaqueous electrolytic solution) (wt %) | 0° C. Discharge Capacity Retention Rate after 85° C. high-temperature charging storage (%) |
|---|---|---|---|---|---|
| Example 11 | 1.2M LiPF6 + 0.05M LiBF4 EC/VC/DMC/MEC (29/1/50/20) | | ethyl (2-trifluoromethylphenyl) carbonate | 1 | 75 |
| Example 12 | 1.2M LiPF6 + 0.05M LiBF4 EC/VC/DMC/MEC (29/1/50/20) | | ethyl (3-trifluoromethylphenyl) carbonate | 1 | 73 |
| Example 13 | 1.2M LiPF6 + 0.05M LiBF4 EC/VC/DMC/MEC (29/1/50/20) | | ethyl (4-trifluoromethylphenyl) carbonate | 1 | 74 |
| Example 14 | 1.2M LiPF6 + 0.05M LiBF4 EC/VC/DMC/MEC (29/1/50/20) | | 2-propynyl (2-trifluoromethylphenyl) carbonate | 1 | 78 |

TABLE 2-continued

| | Composition of Electrolyte Salt Composition of Nonaqueous Electrolyte solution (ratio by volume of solvents) | Compound | | Amount Added (content in nonaqueous electrolytic solution) (wt %) | 0° C. Discharge Capacity Retention Rate after 85° C. high-temperature charging storage (%) |
|---|---|---|---|---|---|
| Example 15 | 1.2M LiPF6 + 0.05M LiBF4 EC/VC/DMC/MEC (29/1/50/20) | (structure) | bis(2-trifluoromethylphenyl) carbonate | 1 | 77 |
| Comparative Example 1 | 1.2M LiPF6 + 0.05M LiBF4 EC/VC/DMC/MEC (29/1/50/20) | — | — | — | 64 |
| Comparative Example 2 | 1.2M LiPF6 + 0.05M LiBF4 EC/VC/DMC/MEC (29/1/50/20) | (structure) | (2-fluorophenyl) methyl carbonate | 1 | 66 |
| Comparative Example 3 | 1.2M LiPF6 + 0.05M LiBF4 EC/VC/DMC/MEC (29/1/50/20) | (structure) | (4-tert-butylphenyl) methyl carbonate | 1 | 64 |

Example 16 and Example 17, Comparative Example 4

A negative electrode sheet was produced, using silicon (elementary substance) (negative electrode active material) in place of the negative electrode active material used in Example 3, Example 11 and Comparative Example 1. Precisely, 80% by mass of silicon (elementary substance) and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto a copper foil (collector), dried, processed under pressure, and blanked into a predetermined size, thereby producing a negative electrode sheet. Coin-type batteries were produced and evaluated in the same manner as in Example 3, Example 11 and Comparative Example 1, except that the negative electrode sheet produced herein was used. The results are shown in Table 3.

TABLE 3

| | Composition of Electrolyte Salt Composition of Nonaqueous Electrolyte solution (ratio by volume of solvents) | Compound | | Amount Added (content in nonaqueous electrolytic solution) (wt %) | 0° C. Discharge Capacity Retention Rate after 85° C. high-temperature charging storage (%) |
|---|---|---|---|---|---|
| Example 16 | 1.2M LiPF6 + 0.05M LiBF4 EC/VC/DMC/MEC (29/1/50/20) | (structure) | 2-trifluoromethylphenyl methanesulfonate | 1 | 68 |
| Example 17 | 1.2M LiPF6 + 0.05M LiBF4 EC/VC/DMC/MEC (29/1/50/20) | (structure) | ethyl (2-trifluoromethylphenyl) carbonate | 1 | 66 |

TABLE 3-continued

| | Composition of Electrolyte Salt Composition of Nonaqueous Electrolyte solution (ratio by volume of solvents) | | Compound | Amount Added (content in nonaqueous electrolytic solution) (wt %) | 0° C. Discharge Capacity Retention Rate after 85° C. high-temperature charging storage (%) |
|---|---|---|---|---|---|
| Comparative Example 4 | 1.2M LiPF6 + 0.05M LiBF4 EC/VC/DMC/MEC (29/1/50/20) | 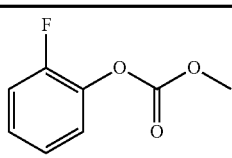 | (2-fluorophenyl) methyl carbonate | 1 | 55 |

Example 18 and Example 19, Comparative Example 5

A positive electrode sheet was produced by changing the positive electrode active material used in Example 3, Example 11 and Comparative Example 1 to LiFePO$_4$ (positive electrode active material) coated with amorphous carbon. Concretely, 90% by mass of LiFePO$_4$ coated with amorphous carbon and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste. The positive electrode mixture paste was applied onto an aluminium foil (collector), dried, processed under pressure and blanked into a predetermined size, thereby producing a positive electrode sheet. Coin-type batteries were produced and evaluated in the same manner as in Example 3, Example 11 and Comparative Example 1, except that the positive electrode sheet thus produced herein was used and that, in battery evaluation, the final charging voltage was changed to 3.6 V and the final discharging voltage was changed to 2.0 V. The results are shown in Table 4.

The lithium secondary batteries of Examples 1 to 15 were all remarkably improved in point of the electrochemical characteristics thereof in a broad temperature range, as compared with the lithium secondary battery of Comparative Example 1 to which the specific compound of the present invention was not added to the nonaqueous electrolytic solution, that of Comparative Example 2 to which (2-fluorophenyl) methyl carbonate described in paragraph [0037] of PTL 1 was added, and that of Comparative Example 3 to which (4-t-butylphenyl) methyl carbonate described in Example 4 in PTL 1.

From the above, it has been clarified that the advantageous effect of the present invention is peculiar to the nonaqueous electrolytic solution of an electrolyte salt dissolved in a nonaqueous solvent that contains from 0.001 to 10% by mass of the specific compound of the present invention.

In addition, from comparison of Examples 16 and 17 with Comparative Example 4, and from comparison of Examples 18 and 19 with Comparative Example 5, the same advantageous effect is seen in the case where silicon (elementary substance) was used as the negative electrode and in the case where a lithium-containing olivine-type iron phosphate was used as the positive electrode. Accordingly, it is obvious that

TABLE 4

| | Composition of Electrolyte Salt Composition of Nonaqueous Electrolyte solution (ratio by volume of solvents) | | Compound | Amount Added (content in nonaqueous electrolytic solution) (wt %) | 0° C. Discharge Capacity Retention Rate after 85° C. high-temperature charging storage (%) |
|---|---|---|---|---|---|
| Example 18 | 1.2M LiPF6 + 0.05M LiBF4 EC/VC/DMC/MEC (29/1/50/20) | 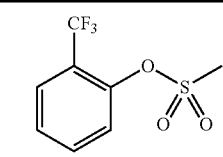 | 2-trifluoro-methylphenyl methanesulfonate | 1 | 82 |
| Example 19 | 1.2M LiPF6 + 0.05M LiBF4 EC/VC/DMC/MEC (29/1/50/20) | 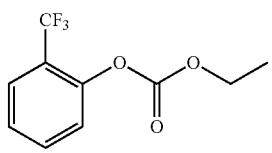 [SMILES: CCOC(=O)Oc1ccccc1C(F)(F)F] | ethyl (2-trifluoro-methylphenyl) carbonate | 1 | 81 |
| Comparative Example 5 | 1.2M LiPF6 + 0.05M LiBF4 EC/VC/DMC/MEC (29/1/50/20) | 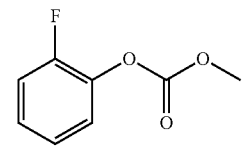 | (2-fluorophenyl) methyl carbonate | 1 | 60 | the advantageous effect of the present invention does not depend on any specific positive electrode or negative electrode.

Further, the nonaqueous electrolytic solution of the present invention has an effect of improving the discharge characteristics of lithium primary batteries in a broad temperature range.

INDUSTRIAL APPLICABILITY

Using the nonaqueous electrolytic solution of the present invention provides energy storage devices excellent in electrochemical characteristics in a broad temperature range. In particular, when the nonaqueous electrolytic solution is used for energy storage devices, such as lithium secondary batteries and the like to be mounted on hybrid electric vehicles, plug-in hybrid electric vehicles, battery electric vehicles, etc., there can be obtained energy storage devices of which the electrochemical characteristics are hardly worsened in a broad temperature range.

The invention claimed is:
1. A nonaqueous electrolytic solution, comprising:
a nonaqueous solvent;
an electrolyte salt dissolved in the nonaqueous solvent; and
a halogenoalkylbenzene compound of formula (I) in an amount of from 0.001 to 10% by mass:

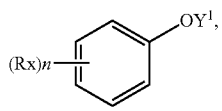

wherein
$Y^1$ represents a substituted or unsubstituted alkenyloxycarbonyl group having from 3 to 9 carbon atoms, a substituted or unsubstituted alkynyloxycarbonyl group having from 4 to 9 carbon atoms, a substituted or unsubstituted aryloxycarbonyl group having from 7 to 12 carbon atoms, a substituted or unsubstituted alkanesulfonyl group having from 1 to 6 carbon atoms, or a substituted or unsubstituted arylsulfonyl group having from 6 to 12 carbon atoms;
$R_X$ represents a fluoroalkyl group having from 1 to 4 carbon atoms; and
n indicates an integer of from 1 to 5;
provided that, when $Y^1$ is a substituted or unsubstituted aryloxycarbonyl group having from 7 to 12 carbon atoms, $R_X$ is a fluoromethyl group, a difluoromethyl group, or a trifluoromethyl group.
2. The nonaqueous electrolytic solution according to claim 1,
wherein the halogenoalkylbenzene compound has $R_X$ at an ortho- or para-position thereof.
3. The nonaqueous electrolytic solution according to claim 1,
wherein the halogenoalkylbenzene compound is at least one selected from the group consisting of 2-propynyl (2-trifluoromethylphenyl) carbonate, phenyl (2-trifluoromethylphenyl) carbonate, bis(2-trifluoromethylphenyl) carbonate, 2-trifluoromethylphenyl methanesulfonate, 2-trifluoromethylphenyl ethanesulfonate, 2-trifluoromethylphenyl benzenesulfonate, 2-trifluoromethylphenyl 2-methylbenzenesulfonate, 2-trifluoromethylphenyl 3-methylbenzenesulfonate, and 2-trifluoromethylphenyl 4-methylbenzenesulfonate.
4. The nonaqueous electrolytic solution according to claim 1,
wherein the nonaqueous solvent comprises a cyclic carbonate and a linear ester.
5. The nonaqueous electrolytic solution according to claim 4,
wherein the cyclic carbonate is at least one selected from the group consisting of ethylene carbonate, propylene carbonate, 1,2-butylene carbonate, 2,3-butylene carbonate, 4-fluoro-1,3-dioxolan-2-one, trans or cis-4,5-difluoro-1,3-dioxolan-2-one, vinylene carbonate, and vinylethylene carbonate.
6. The nonaqueous electrolytic solution according to claim 5, wherein the linear ester is methyl ethyl carbonate.
7. The nonaqueous electrolytic solution according to claim 4,
wherein the linear ester is at least one selected from the group consisting of an asymmetric linear carbonate, a symmetric linear carbonate, a pivalate and a linear carboxylate,
wherein the asymmetric linear carbonate is selected from the group consisting of methyl ethyl carbonate, methyl propyl carbonate, methyl isopropyl carbonate, methyl butyl carbonate and ethyl propyl carbonate;
the symmetric linear carbonate is selected from the group consisting of dimethyl carbonate, diethyl carbonate, dipropyl carbonate and dibutyl carbonate;
the pivalate is selected from the group consisting of methyl pivalate, ethyl pivalate and propyl pivalate; and
the linear carboxylate is selected from the group consisting of methyl propionate, ethyl propionate, methyl acetate and ethyl acetate.
8. The nonaqueous electrolytic solution according to claim 4,
wherein the linear ester is at least methyl group-having linear carbonate selected from the group consisting of dimethyl carbonate, methyl ethyl carbonate, methyl propyl carbonate, methyl isopropyl carbonate, methyl butyl carbonate, methyl propionate, methyl acetate and ethyl acetate.
9. The nonaqueous electrolytic solution according to claim 4, wherein the cyclic carbonate is ethylene carbonate, and the linear ester is selected from the group consisting of methyl ethyl carbonate, methyl propyl carbonate, methyl isopropyl carbonate, methyl butyl carbonate and ethyl propyl carbonate.
10. The nonaqueous electrolytic solution according to claim 1, wherein $Y^1$ has at least one hydrogen atom substituted with a halogen atom.
11. The nonaqueous electrolytic solution according to claim 1, wherein $Y^1$ has at least one hydrogen atom substituted with a fluorine atom.
12. The nonaqueous electrolytic solution according to claim 1, wherein n is 1 or 2.
13. An energy storage device, comprising:
a positive electrode;
a negative electrode; and
the nonaqueous electrolytic solution according to claim 1.
14. The energy storage device according to claim 13,
wherein the positive electrode comprises a lithium complex oxide, and
the negative electrode comprises a carbon material having a graphite-type crystal structure.

15. An additive, comprising:
a halogenoalkylbenzene compound of formula (I):

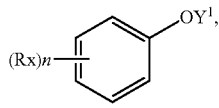
(I)

wherein
$Y^1$ represents a substituted or unsubstituted alkenyloxycarbonyl group having from 3 to 9 carbon atoms, a substituted or unsubstituted alkynyloxycarbonyl group having from 4 to 9 carbon atoms, a substituted or unsubstituted aryloxycarbonyl group having from 7 to 12 carbon atoms, a substituted or unsubstituted alkanesulfonyl group having from 1 to 6 carbon atoms, or a substituted or unsubstituted arylsulfonyl group having from 6 to 12 carbon atoms;
$R_x$ represents a fluoroalkyl group having from 1 to 4 carbon atoms; and
n indicates an integer of from 1 to 5;
provided that, when $Y^1$ is a substituted or unsubstituted aryloxycarbonyl group having from 7 to 12 carbon atoms, $R_x$ is a fluoromethyl group, a difluoromethyl group, or a trifluoromethyl group.

16. The additive according to claim 15, wherein $Y^1$ has at least one hydrogen atom substituted with a halogen atom.

17. The additive according to claim 15, wherein $Y^1$ has at least one hydrogen atom substituted with a fluorine atom.

18. A trifluoromethylbenzene compound of formula (II):

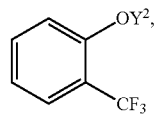
(II)

wherein $Y^2$ represents a substituted or unsubstituted alkenyloxycarbonyl group having from 3 to 9 carbon atoms, a substituted or unsubstituted alkynyloxycarbonyl group having from 4 to 9 carbon atoms, a substituted or unsubstituted aryloxycarbonyl group having from 7 to 12 carbon atoms, a substituted or unsubstituted alkanesulfonyl group having from 1 to 6 carbon atoms, or a substituted or unsubstituted arylsulfonyl group having from 6 to 12 carbon atoms.

19. The trifluoromethylbenzene compound according to claim 18, wherein $Y^2$ has at least one hydrogen atom substituted with a halogen atom.

20. The trifluoromethylbenzene compound according to claim 18, wherein $Y^2$ has at least one hydrogen atom substituted with a fluorine atom.

* * * * *